United States Patent [19]

Curley et al.

[11] 4,427,661

[45] Jan. 24, 1984

[54] FLUORINATED CYCLIC HEXAPEPTIDE SOMATOSTATIN ANALOGS

[75] Inventors: Paul E. Curley, North Wales; Ralph F. Hirschmann, Blue Bell, both of Pa.

[73] Assignee: Merck & Co., Inc., Rahway, N.J.

[21] Appl. No.: 403,942

[22] Filed: Jul. 30, 1982

[51] Int. Cl.$^3$ .................. C07C 103/52; A61K 37/02
[52] U.S. Cl. ........................ 424/177; 260/112.5 S
[58] Field of Search ................ 260/112.5 S; 424/177

[56] References Cited

U.S. PATENT DOCUMENTS 4,235,886 11/1980 Freidinger et al. .............. 424/177
4,310,518 1/1982 Freidinger et al. .............. 424/177

OTHER PUBLICATIONS

*J. Org. Chem.*, 44 p. 771, Kollonitsch et al. (1979)(I).
*J. American Chem. Soc.*, 92, p. 7494, Kollonitsch et al. (1970)(II).
*Biochem.*, 4, p. 2501, Izumiya et al., (1965).

*Primary Examiner*—Delbert R. Phillips
*Assistant Examiner*—F. T. Moezie
*Attorney, Agent, or Firm*—David L. Rose; Mario A. Monaco

[57] ABSTRACT

Fluorinated somatostatin analogs are prepared wherein a cyclic hexapeptide contains a secondary amino acid which replaces seven of the ring amino acids of somatostatin and the Lys side chain is monofluorinated in the $\gamma$ or $\delta$ positions. The cyclic hexapeptides are easier to synthesize, have a longer duration of activity, and many have a greater level of activity than somatostatin. The compounds have the properties of inhibiting the release of glucagon, growth hormone and insulin. Certain of the compounds also are capable of inhibiting the release of gastric acid secretions. The compounds are particularly useful in the treatment of acromegaly, diabetes, diabetic retinopathy and peptic ulcers. These cyclic hexapeptides are prepared by the solid phase method.

9 Claims, No Drawings

FLUORINATED CYCLIC HEXAPEPTIDE SOMATOSTATIN ANALOGS

BACKGROUND OF THE INVENTION

Somatostatin is a tetradecapeptide incorporating a cyclic dodecapeptide, having the structure:

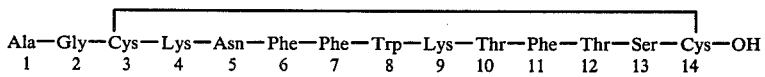

and has the properties of inhibiting the release of growth hormone, inhibiting the release of insulin and glucagon and reducing gastric secretion. Somatostatin itself has a short duration of action because it is inactivated, inter alia, by amino peptidases and carboxypeptidases present in vivo. This problem of the short duration of action has been partially solved in the prior art by preparing derivatives of somatostatin which have low solubility, thus attaining a slow release on subcutaneous injection. Once dissolved, however, the derivatives are no more stable to inactivation by aminopeptidases and carboxypeptidases than somatostatin itself.

SUMMARY OF THE INVENTION

The present invention provides for fluorinated cyclic hexapeptides which are derivatives of somatostatin in which, inter alia, seven of the ring amino acids are replaced by a secondary amino acid, both of the exocyclic amino acids are removed, and the Lys side chain is monofluorinated at the γ or positions. Further substitution and reaction of the remaining amino acids is also described. The cyclic hexapeptides inhibit the release of glucagon, growth hormones and insulin, and inhibit the release of gastric acid secretions. Specifically the compounds may preferentially inhibit the release of growth hormones without effecting the level of gastric secretions or without effecting the level of gastric secretions, insulin and glucogon, or the compounds may inhibit the release of gastric acid secretions. Thus, the compounds have a more selective biological activity than somatostatin. The cyclic hexapeptide structure of the instant compounds also have a longer duration of activity than somatostatin. As such the instant cyclic hexapeptides are useful for the treatment of acromegaly, diabetes, diabetic retinopathy and peptic ulcers.

Thus, it is an object of the present invention to describe the fluorinated cyclic hexapeptide somatostatin analogs. A further object is to describe procedures for the preparation of such fluorinated cyclic hexapeptides. A still further object is to describe the use of such compounds in the treatment of acromegaly, diabetic retinopathy and peptic ulcers. Further objects will become apparent from reading the following description.

DESCRIPTION OF THE INVENTION

The compounds of the instant invention are best realized in the following structural formulae:

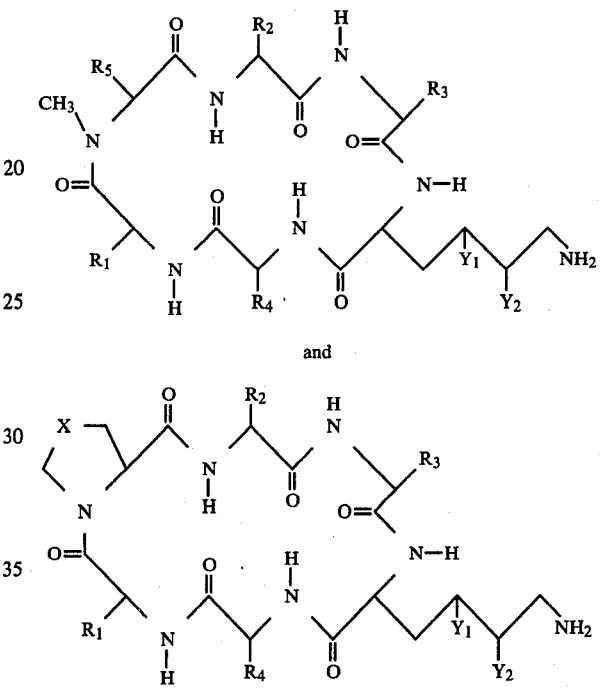

-continued wherein
$Y_1$ and $Y_2$ are hydrogen or fluorine provided $Y_1$ and $Y_2$ are not the same;
X is $(CH_2)_m$ wherein m is 0, 1 or 2 or sulfur;
$R_1$ and $R_2$ are independently loweralkyl, benzyl, substituted benzyl where the substituent may be one or two of loweralkyl, halogen, hydroxy, amino, nitro or loweralkoxy; and loweralkyl substituted with a 5- or 6-membered heterocyclic ring;
$R_3$ is 3-indolylmethyl or substituted 3-indolylmethyl wherein the substituent may be loweralkyl, loweralkoxy, or halogen;
$R_4$ is loweralkyl, hydroxyloweralkyl, benzyl, carboxyloweralkyl, aminoloweralkyl or substituted benzyl wherein the substituent may be loweralkyl, loweralkoxy, hydroxy, halogen, amino or nitro; and
$R_5$ is hydrogen, loweralkyl, benzyl, or substituted benzyl wherein the substituent is loweralkyl, loweralkoxy, hydroxy, halogen, amino or nitro.

The term "loweralkyl" when used in the instant application is intended to represent those alkyl groups either straight or branched chain, which have from 1-5 carbon atoms. Examples of such alkyl groups are methyl, ethyl, propyl, iso-propyl, butyl, sec-butyl, pentyl and the like.

The term "loweralkoxy" is intended to include those alkoxy groups of from 1 to 5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the instant compounds there are several assymetric centers which will lead to the existence of optical isomers for such compounds. In the instant invention, for each of the assymetric centers of the various amino acids which make up the instant cyclic hexapeptides, both the D and L configurations, as well as diastereomers therein included, are intended to be encompassed.

It will be appreciated by those skilled in the art that when $R_1$ and $R_2$ are benzyl, $R_3$ is indolylmethyl, $Y_1$ and $Y_2$ are hydrogen and $R_4$ is 1-hydroxyethyl, the 7, 8, 9, 10 and 11 amino acids of somatostatin (Phe-Trp-Lys-Thr-Phe-) are represented, and the secondary amino acid, represented by N-methyl alanine when $R_5$ is methyl and by proline when X is methylene, has taken the place of the remainder of the somatostatin amino acids. Thus, using the above definitions of the substituent groups, the following representative cyclic hexapeptide analogs of somatostatin are formed:

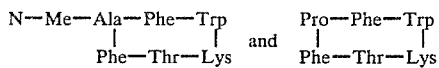

The preferred embodiments of the cyclic hexapeptides of this invention are realized in the foregoing structural formula wherein $Y_1$ and $Y_2$ are as defined above;

$R_1$ and $R_2$ are as defined above;

$R_3$ is 3-indolylmethyl or substituted indolylmethyl wherein the substituent is methoxy or fluoro;

$R_4$ is methyl, ethyl, hydroxy methyl or hydroxy ethyl; and $R_5$ is methyl or hydrogen.

Further preferred embodiments are realized when Y is methylene;

$Y_1$, $Y_2$, $R_1$ and $R_2$ are as defined above;

$R_3$ is 3-indolylmethyl;

$R_4$ is hydroxyethyl; and $R_5$ is methyl.

The preferred $R_1$ and $R_2$ groups are loweralkyl, benzyl or substituted benzyl where the substituent is loweralkyl, halogen, hydroxy, amino, nitro or alkoxy.

Included within these preferred compounds are:

Cyclo-(N-Me-Ala-Tyr-D-Trp-γ-F-Lys and δ-F-Lys-Thr-Phe)

Cyclo-(N-Me-Ala-Phe-D-Trp-γ-F-Lys and δ-F-Lys-Thr-Phe)

Cyclo-(N-Me-Ala-Phe-L-Trp-γ-F-Lys and δ-F-Lys-Thr-Phe)

Cyclo-(N-Me-Ala-Phe-D-Trp-γ-F-Lys and δ-F-Lys-Thr-p-Cl-Phe)

Cyclo-(N-Me-Ala-Phe-D-5-F-Trp-γ-F-Lys and δ-F-Lys-Thr-Phe)

Cyclo-(N-Me-Ala-Phe-L-5-F-Trp-γ-F-Lys and δ-F-Lys-Thr-Phe)

Cyclo-(N-Me-Ala-Phe-D-Trp-γ-F-Lys and δ-F-Lys-Ser-Phe)

Cyclo-(N-Me-Ala-Tyr-D-Trp-γ-F-Lys and δ-F-Lys-Val-Phe)

Cyclo-(Ser-Phe-D-Trp-γ-F-Lys and δ-F-Lys-Thr-Phe)

Cyclo-(N-Me-Ala-Phe-D-Trp-γ-F-Lys and δ-F-Lys-Val-Phe)

Cyclo-(Pro-Tyr-D-Trp-γ-F-Lys and δ-F-Lys-Thr-Phe)

Cyclo-(Pro-Phe-D-Trp-γ-F-Lys and δ-F-Lys-Thr-Phe)

Cyclo-(Pro-Phe-L-Trp-γ-F-Lys and δ-F-Lys-Thr-Phe)

Cyclo-(Pro-Phe-D-Trp-γ-F-Lys and δ-F-Lys-Thr-p-Cl-Phe)

Cyclo-(Pro-Phe-D-5-F-Trp-γ-F-Lys and δ-F-Lys-Thr-Phe)

Cyclo-(Pro-Phe-L-5-F-Trp-γ-F-Lys and δ-F-Lys-Thr-Phe)

Cyclo-(Pro-Phe-D-Trp-γ-F-Lys and δ-F-Lys-Ser-Phe)

In the instant application several abbreviated designations are used for the amino acid components, certain preferred protecting groups, reagents and solvents. The meanings of such abbreviated designations are given in Table I.

TABLE I

| Abbreviated Designation | Amino Acid |
|---|---|
| Lys | L-lysine |
| Phe | L-phenylalanine |
| Trp | L-tryptophan |
| D-Trp | D-tryptophan |
| Thr | L-threonine |
| Aha | 7-aminoheptanoic acid |
| Tyr | L-tyrosine |
| Val | L-valine |
| Abu | L-α-aminobutyric acid |
| Ser | L-serine |
| Asn | L-asparagine |
| Pro | L-proline |
| Asu | D or L-aminosuberic acid |
| Cys | L-cysteine |

| Abbreviated Designation | Protecting Groups |
|---|---|
| INOC | isonicotinyloxycarbonyl |
| BOC | tert-butyloxycarbonyl |
| OMe | methyl ester |
| Bu | tert-butyl |
| CBZ | benzyloxycarbonyl |
| Bzl | benzyl |
| 2-Cl—CBZ | 2-chlorobenzyloxycarbonyl |
| Acm | acetamidomethyl |
| Me | methyl |
| FMOC | α-fluorenylmethyloxycarbonyl |

| Abbreviated Designation | Activating Groups |
|---|---|
| ONp | p-nitrophenyl ester |
| HSE | N—hydroxysuccinimide ester |
| HBT | 1-hydroxybenzotriazole |

| Abbreviated Designation | Condensing Agents |
|---|---|
| DCCI | dicyclohexylcarbodiimide |

| Abbreviated Designation | Reagents |
|---|---|
| TFA | trifluoroacetic acid |
| TEA | triethylamine |
| DIPEA | diisopropylethylamine |

| Abbreviated Designation | Solvents |
|---|---|
| EPAW | ethyl acetate-pyridine-acetic acid-water |
| BAW | butanol-acetic acid-water |
| CMW | chloroform-methanol-water |

TABLE I-continued

| | |
|---|---|
| DMF | dimethylformamide |
| THF | tetrahydrofuran |
| CMA | chloroform-methanol-acetic acid |

Another aspect of the instant invention is the fluorinated lysine starting material used to prepare the instant fluorinated cyclic hexapeptides. Specifically, the γ-fluorinated compound is novel. In addition, the α- and ε protected derivatives of γ-fluorolysine are likewise novel, such as the compound protected with CBZ, 2-Cl-CBZ, BOC, INOC or FMOC groups.

The γ-fluorolysine is prepared by fluorinating lysine using either fluorodehydroxylation or photofluorination techniques. In the fluorodehydroxylation reaction the starting material must have a hydroxy at the position to be fluorinated and, in the case of lysine, the carboxy must be protected to prevent lactonization. Hydrogen fluoride and sulfur tetrafluoride are used with a protected γ-hydroxylysine amide to prepare the γ-fluoro compound according to the general procedure of Kollonitsch et al., *J. Org. Chem.*, 44, 771 (1979).

The γ-fluorolysine may also be prepared by photofluorination in hydrogen fluoride with trifluoromethylhypofluorite although this procedure usually also prepares the γ-fluoro compound. The mixture of compounds yields both of the starting materials used to prepare the instant compounds and they may be separated prior to the formation of the instant cyclic hexapeptide, or, as one done in at least one case. The mixture of γ- and δ-fluorolysine compounds is used to prepare the corresponding mixture of fluoro cyclic hexapeptides, and the two fluoro isomers then separated. A general photofluorination procedure is given in Kollonitsch et al., *J. Am. Chem. Soc.*, 92, 7494 (1970).

In accordance with the present invention, the novel fluorinated cyclic hexapeptide somatostatin analogs are prepared by cyclizing corresponding linear peptides. The linear peptides are prepared by using the solid phase sequential synthesis technique. Accordingly, the process for preparing the fluorinated cyclic hexapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic hexapeptide through the formation of an amide bond; (e) removing any side chain blocking groups.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example D-Trp can react with t-butyl carbonium ions which are formed when BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1–2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as for example, as the carboxylic ester of the resin-bonded benzyl chloride present in chloromethyl-substituted polystyrene-divinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarly employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxycarbonyl (BOC) for protecting the α-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The OH group of Thr and Ser can be protected by the Bzl group and the ε-amino group of Lys can be protected by the INOC group, the 2-chlorobenzyloxycarbonyl (2-Cl-CBZ) group or the benzyloxycarbonyl (CBZ) group. In the case of Lys, it is preferred to protect the ε-amino group with 2-Cl-CBZ or CBZ group as these groups are removed simultaneously with the Bzl groups by treatment with HF after the linear peptide has been cyclized. The INOC group is not removed by HF and requires an additional treatment with Zn. Neither group is affected by TFA, used for removing BOC protecting group. After the linear peptide is cyclized, the protective groups, such as 2-Cl-CBZ, CBZ and Bzl, are removed by treatment with HF.

After the linear peptide has been formed on the solid phase resin, it may be removed from the resin by a variety of methods which are well known in the art. For example, the peptide may be cleaved from the resin with hydrazine and thus directly form the peptide hydrazide which may be subsequently cyclized via the azide to the desired cyclic peptide. The hydrazide is converted to the corresponding azide by reaction with a reagent which furnishes nitrous acid in situ. Suitable reagents for this purpose include a lower alkyl nitrite (e.g., t-butyl nitrite, isoamyl nitrite), or an alkali metal nitrite salt (e.g., sodium nitrite, potassium nitrite) in the presence of a strong acid such as hydrochloric, phosphoric, etc. This reaction is carried out in the presence of either water and/or a non-aqueous solvent such as dimethylformamide, tetrahydrofuran, dioxane, chloroform, methylene chloride, etc., at a temperature between about −40° C. and +20° C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the hydrazide which may then be cyclized, via the azide, to the desired cyclic peptide. The preferred method for cleaving the peptide from the resin in the present invention is the use of hydrazine.

As reference Table II will show, one preferred overall procedure for preparing the desired cyclic peptides of the present invention involves the stepwise synthesis of the linear peptide on a solid phase resin. More specifically, in the process for preparing:

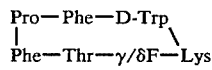

the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the Phe is completed on the resin, the protecting group BOC is removed by treatment with TFA in CH$_2$Cl$_2$. The subsequent amino acids are attached, in the form of BOC-amino acid, using DCCI as the condensing agent or an active ester such as ONp. After the desired linear peptide has been prepared, the N-terminal amino group is selectively deblocked and the peptide is removed from the resin by treatment with hydrazine. The resulting linear peptide hydrazide with the N-terminal amino group deblocked having the amino acid sequence:

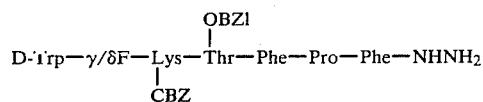

is treated with isoamyl nitrite in acid pH to form the corresponding azide. The azide solution is diluted with solvent and neutralized with an organic base. The linear peptide cyclizes to form:

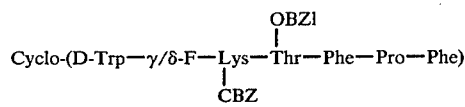

During the cyclization the "pH" is checked and maintained at neutral by the addition of organic base. The "pH" in organic solvent is determined by the application of an aliquot of the solution to moistened narrow range pH paper.

After the linear peptide is cyclized, the protective groups, CBZ and BZl, are removed by treatment with HF in the presence of anisole. The crude cyclic peptide obtained is purified chromatographically, preferably with column chromatography on silica gel. The elution solvent is generally an organic solvent to mixtures thereof which is selected by analyzing aliquots of the material using thin layer chromatography.

TABLE II

The reaction scheme for the preparation of two of the cyclic hexapeptides of this invention is outlined in the following series of reactions.

Following is the reaction scheme for preparing:

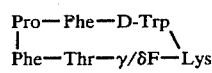

in which the compounds were prepared using a mixture of the γ-F and δ-F-Lys starting materials and the individual cyclic hexapeptides were separated at the end of the reaction sequence. However, the individual γ-F-Lys and δ-F-Lys starting materials could be employed with equivalent results.

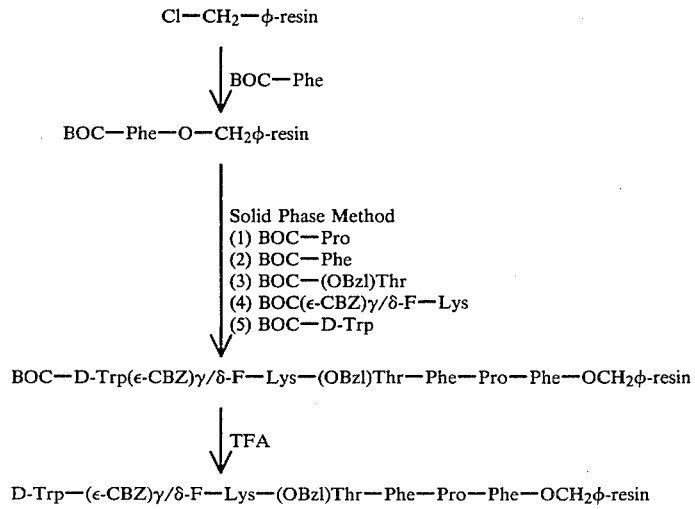

-continued

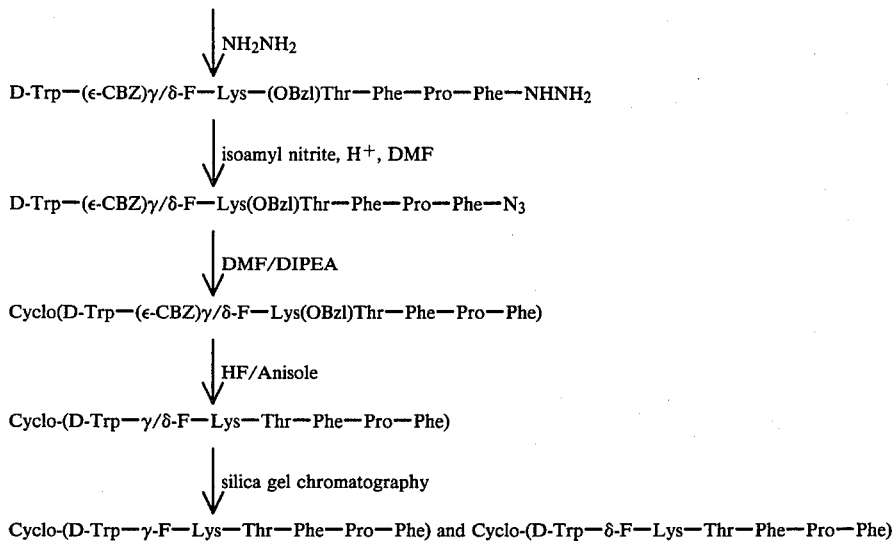

The following Examples are given to illustrate the methods used to carry out the present invention. It is to be understood that these Examples are given for purposes of illustration and not limitation.

EXAMPLE 1

Preparation of
D-Trp-(ε-CBZ)γ/δ-F-Lys-(OBzl)Thr-Phe-Pro
Phe-OCH₂O-resin

Chloromethyl resin (2% cross-linked Merrifield resin), 862.0 g. (2.37 moles), having 2.75 meq. chlorine/g., and 607.0 g. (2.37 moles, 1 equivalent) of BOC-Phe were added to 4320 ml. of peroxide-free tetrahydrofuran. The mixture was stirred in an oil bath at 80° C. bath temperature for 45 minutes. Triethylamine, 310.0 ml., was added and the reaction mixture stirred at 80° C. bath temperature for 70 hours, cooled to 25° C. and transferred to a stirred solid phase reaction column with 2000 ml. of tetrahydrofuran. After removal of the solvent, the resin was washed using the stirred column with:

3×2000 ml. of tetrahydrofuran
4×5170 ml. of ethanol
1×5170 ml. of acetic acid
3×5170 ml. of water
3×5170 ml. of methanol
3×5170 ml. of chloroform The BOC-Phe-O-CH₂-φ-resin was dried in vacuo at 25° C. for 16 hours, giving 1203 g. of BOC-Phe-O-CH₂-φ-resin containing 1.2 mmole of phenylalanine/g. of resin.

BOC-Phe-O-CH₂φ-resin (2.13 g.; 2.0 mmole) was carried through the procedures in Tables III and IV using 2 deblockings (2 minutes and 25 minutes) with 25% TFA in methylene chloride and from 1.2 to 2.5 equivalents of BOC-amino acid in the required sequence until the desired BOC-hexapeptide-O-CH₂φ-resin was obtained.

DCCI was used as the sole coupling agent in every step.

The coupling of each amino acid proceeded smoothly. Best yields were obtained when the coupling was repeated in each step. When the coupling was repeated, the initial two chloroform washes, the deblocking step and the succeeding three chloroform washes were all omitted and replaced by a single chloroform wash. Repeat couplings were carried out in DMF using DCCI activation in the presence of HBT.

The coupling reactions were carried out in methylene chloride, freshly degassed DMF or a mixture of these two solvents. The N-terminal amino group was blocked with a BOC group in each case; the hydroxy group of Thr was blocked with Bzl and the ε-amino group of the γ- and δ-fluoro Lys with CBZ.

When the desired BOC-hexapeptide-2-CH₂-φ-resin was obtained, the N-terminal BOC group was removed by the terminal deblocking procedure set forth in Table V.

TABLE III

| Solvent or reagent (number of treatments or washes) | CHCl₃ (2) | 25% TFA in CH₂Cl₂ | CHCl₃(3) | NEt₃— CH₂Cl₂ (1:9) (2) | CHCl₃(3) CH₂Cl₂(3) | BOC AA in CH₂Cl₂ DMF or a mixture of both | 0.5M DCCI in CH₂Cl₂ | DMF(1) MeOH(1) MeOH(1) CHCl₃(2) |
|---|---|---|---|---|---|---|---|---|
| Vol. in ml. | 40 | 20 | 40 | 40 | 40 | 25 | 10 | 40 |
| Time in min. | 5 | 2 and 25 | 2 | 5 and 5 | 2 | 5 | 120–960 | 2 |

TABLE IV

| Protected Amino Acid | Solvent Ml. |
|---|---|
| BOC—Pro (0.645 g.) | 25 ml. CH₂Cl₂ |
| BOC—Phe (0.795 g.) | 25 ml. CH₂Cl₂ |
| BOC (OBZ)Thr (0.927 g.) | 25 ml. CH₂Cl₂ |
| Recouple with 0.612 g of BOC(OBZ—Thr) | 10 ml. DMF |
| BOC—(CBZ)γ/δ-F—Lys (0.96 g.) + HBT H₂O (0.46 g.) | |
| BOC—D-Trp (0.91 g.) | 20 ml. CH₂Cl₂, 5 ml. DMF |
| Recouple with BOC—D-Trp (0.61 g) + HBT H₂O (0.46 g) | 10 ml. DMF |

TABLE V
TERMINAL DEBLOCKING PROGRAM

| Solvent or reagent (number of treatments or washes) | CHCl$_3$(1) | 25% TFA in CH$_2$Cl$_2$ + 1% Ethanedithiol (2) | CHCl$_3$ (3) | MeOH(2) CH$_2$Cl$_2$(1) MeOH(2) CH$_2$Cl$_2$(2) |
|---|---|---|---|---|
| Vol. in ml. | 40 | 40 | 40 | 40 |
| Time in minutes | 5 | 2 and 25 | 2 | 2 |

After the procedures of Tables III, IV and V were completed, the blocked hexapeptide-OCH$_2$O-resin is dried overnight and weighs 3.80 g.

EXAMPLE 2
Preparation of
D-Trp-(ε-CBZ)γ/δ-F-Lys-(OBzl)Thr-Phe-Pro Phe-NHNH$_2$ The resin from Example 1 was combined with 20 ml. of methanol and 10 ml of hydrazine and stirred at room temperature for 37 minutes. The insoluble resin was removed by filtration, and washed with methanol. Water was added and the mixture again evaporated. 450 ml of water was used to wash the peptide and the residue was placed under high vacuum overnight to remove all volatile materials. The residue weighed 1.89 g.

EXAMPLE 3
Preparation of
D-Trp-(ε-CBZ)γ/δ-F-Lys-(OBzl)-Thr-Phe-Pro-Phe N$_3$ The material from Example 2 was combined with 20 ml. of degassed dimethylformamide under a blanket of nitrogen and cooled to −10° C., and 1.70 ml of 5.15 M hydrogen chloride in tetrahydrofuran was added. The solution is cooled to −25° C. and 0.30 ml isoamyl nitrite was added. The completion of the reaction was followed by thin layer chromatography and the disappearance of the hydrazide starting material.

EXAMPLE 4
Preparation of
Cyclo(D-Trp-(ε-CBZ)γ/δ-F-Lys-(O-Bzl)Thr-Phe-Pro-Phe)

The azide compound of Example 3 was added to 1.5 l. of degassed dimethylformamide, precooled to −25° C., the pH adjusted to 7.0–7.2 with DIPEA, and the reaction mixture placed in the freezer overnight. The pH was readjusted to 7.0–7.2 if necessary. After about 14 hours, the mixture was stored for 24 hours at 5° C. Thin layer chromatography indicated that the reaction was completed. The mixture was concentrated to a small volume, and the residue triturated with 100 ml. of water and filtered. The filtered solid was washed with water and dried in vacuo overnight affording 1.80 g of product.

EXAMPLE 5
Preparation of
Cyclo(D-Trp-γ/δ-F-Lys-Thr-Phe-Pro-Phe)

1.80 G. of the protected cyclic hexapeptide of Example 4 was combined in a teflon lined chamber with 3 ml. of anisole. The chamber was then evacuated and filled with 35 ml of liquid hydrogen fluoride at the temperature of the dye ice/acetone bath. The temperature was raised to 0° C. and stirring continued for ½ hour. The hydrogen fluoride was allowed to evaporate and the residue placed in vacuo. The residue was washed 4 times with petroleum ether and with ethyl acetate and filtered affording 1.38 g. of product after drying overnight.

EXAMPLE 6
Cyclo(Pro-Phe-D-Trp-γ-F-Lys-Thr-Phe) and cyclo (Pro-Phe-D-Trp-δ-F-Lys-Thr-Phe)

The crude cyclic product mixture containing both the γ-fluoro and δ-fluoro peptides (1.3 g) was chromatographed using silica gel 60 (390 g). Elution with CMA (90-10-1) gave the δ-fluoro compound (290 mg) after evaporation, dissolution in dilute acetic acid and lyophilization. Further elution yielded 250 mg of the γ-fluoro compound. Intermediate fractions gave 600 mg of product as a mixture of γ-fluoro and δ-fluorolysine containing analogs. The isomeric peptides were characterized especially well by nuclear magnetic resonance spectroscopy. Decoupling experiments for the protons of the lysine side chain gave proof as to the structures of the γ-fluoro and δ-fluoro compounds. In all other aspects the spectra were very similar to each other and to that of the unfluorinated compound. Amino acid analysis after acid hydrolysis of the γ-fluoro compound indicated the presence of the two diastereomers ("erythro" and "threo") of γ-F-lysine in a ratio of 3:1. The two diastereomeric hexapeptides (containing "erythro" and "threo"-γ-F-lysine) also showed a slight difference in retention time during HPLC (16.13 minutes and 16.79 minutes). No assignments were made to which isomer was the major component. Amino acid and HPLC analyses of the δ-fluoro compound do not detect the presence of two isomers.

Following the above procedure, and by modifying only the selection and order of amino acids in the process of Example 1, there are prepared other cyclic hexapeptides of this invention.

The instant cyclic hexapeptide analogs of somatostatin are tested and compared with the effects of somatostatin in tests for the inhibition of growth hormone, insulin and glucagon. The tests are described as follows:

Growth Hormone—in vitro

Rat pituitaries were isolated according to the procedures of Vale and Grant "In vitro Pituitary Hormone Secretion Assay for Hypophysioprivic Substances" in Methods in Enzymology. Vol.XXXVII, eds. O'Malley, B. W. and Hardman, J. G. (Academic Press, Inc., New York) pp. 5–93 (1975).

After 4 days in culture, the cells were washed and incubated for 4 hours in Dulbecco modified Eagle's medium in the presence or absence of graded doses of each analog or somatostatin. The medium was then collected for subsequent growth hormone determination by a double antibody radioimmunoassay for rat growth hormone.

Insulin and Glucagon

Analogs of somatostatin were compared to somatostatin in their ability to decrease the levels of portal vein glucagon and insulin in anesthetized rats. Male Sprague-Dawley rats (Charles River CD) weighing 160–200 g were anethetized with urethane (150 mg/100 g of body weight; Aldrich). Saline or peptides were administered via the external jugular vein. After 5 minutes, the portal vein was exposed, and blood was collected via syringe containing 3 mg of EDTA and placed in chilled tubes containing 100 μl of Trasylol (FBA Pharmaceuticals) for subsequent hormone analysis. Plasma levels of glucagon were determined by the method of Faloona and Unger, *Methods of Hormone Radioimmunoassay*, Jaffe and Behrman (Eds), Academic Press, New York, Vol. II, pp. 257-527 (1976), utilizing glucagon antisera 30K obtained from R. Unger (Dallas, Tx). Plasma levels of insulin were determined by a modification of the procedure of Herbert et al., *J. Clin. Endocrinol. Metab.*, 25, 1375-1384 (1965).

The test results for some of the compounds of this invention are recorded below with the results for somatostatin listed first and given the arbitrary value of 1. The results for the instant compounds are given as multiples or fractions of the effect of somatostatin. The numbers in parentheses are the fiducial limits for the number preceding. The first of the instant compounds listed is the compound prepared in Example 1-5. The compound is written slightly different, however, to conform to the order of the amino acids found in somatostatin.

| Activity of Cyclic hexapeptide Analogs of Somatostatin | | | |
|---|---|---|---|
| Compound | Growth Hormone Release Inhibition In Vitro | Insulin Inhibition In Vivo | Glucagon Inhibition In Vivo |
| Somatostatin | 1 | 1 | 1 |
| Cyclo(Pro—Phe—D-Trp—γ-F—Lys—Thr—Phe) | 2.17 (1.08, 4.86) | 2.76 (1.63, 4.45) | 1.64 (0.78, 6.02) |
| Cyclo(Pro—Phe—D-Trp—δ-F—Lys—Thr—Phe) | 2.25 (1.18, 4.78) | 2.10 (1.25, 3.16) | 2.57 (1.09, 41.42) |

The effects of the instant cyclic hexapeptide analogs of somatostatin on gastric acid secretions are determined by the following procedure.

Compounds were tested for their ability to inhibit pentagastrin evoked gastric secretion in the chronic fistula dog. Female beagle dogs with a chronic gastric fistula were given pentagastrin (2.5 μg./kg./hour, i.v. from −60 to 120 min.) and gastric outputs were collected via the fistula cannula. Samples were analyzed at 30 minute intervals for volume (ml.) and titratable acid (mEq/L) (Titration to pH 7 with 0.01 N NaOH); total acid output (mEq) was calculated as the production of output volume and acid concentration. Test compounds were infused at a constant rate from 0 to 60 minutes. Data have been expressed as percent change of total acid output relative to a placebo trial in the same animals.

In the following data, the results for somatostatin are given first for comparison purposes.

EXAMPLE 7

4-Fluoro-L-lysine by fluorodehydroxylation

N,N'-Dicarbobenzyloxy-γ-hydroxy-L-lysine amide (2.0 g, 4.65 mmol) (described by Izumiya et al., *Biochem*, 4, 2501 (1965)) was placed in a Kel-F® reactor and anhydrous hydrogen fluoride (40 ml) was condensed at −78° C. Sulfur tetrafluoride (1.8 ml, 31 mmol) was condensed at −78° C. in a graduated tube attached to the reaction vessel. The cooling bath was removed and sulfur tetrafluoride was transferred into the reaction solution (cooled at −78° C.) by evaporation. The mixture was stirred at −78° C. for 5 hours and allowed to stand overnight. Hydrogen fluoride was removed by a stream of nitrogen and the residue dissolved in 30 ml of 2.5 N HCl. Insoluble material was filtered and the filtrate evaporated to dryness in vacuo to yield 1.01 g of crude 4-fluoro-L-lysine amide contaminated with unreacted 4-hydroxy-L-lysine amide. The crude amide (1.4 g) was hydrolyzed in 90 ml 2.5 N HCl by refluxing for 1.5 hours, the reaction solution was evaporated to dryness and separated by ion exchange chromatography (Dowex 50-X8 resin, 120 ml, H+ form, washed first with 500 ml water and eluted with 2.5 N HCl). The 4-hydroxy-L-lysine in strong acid formed the lactone which, being a strong base, was not eluted from the resin with 2.5 N HCl. 4-Fluoro-L-lysine.2HCl was obtained in 52% yield and >90% purity, $[\alpha]_D^{25}+16.8°$ (3% in 2.5 N HCl. The monohydrochloride was obtained in 76% yield by dissolving the dihydrochloride in 15 volumes methanol and adding 50% molar excess pyridine. This material was recrystallized from isopropanol/water (2:1) to give a product with a rotation of $[\alpha]_D^{25}+25°$ (2% in 2.5 N HCl) mp: 210° (discoloration), 215°-17° (d).

EXAMPLE 8

4-Fluoro-L-lysine by photofluorination

A Kel-F® lined reactor and the general photofluorination method described in Kollonitsch et al., *J. Am. Chem. Soc.*, 92, 7494 (1970)) was used to fluorinate lysine. The light source was a Hanovia mercury-xenon 2,500 W lamp fitted into a quartz projector manufactured by Kratos Inc., Schoeffel Instrument Division. The apparatus was swept with nitrogen and all operations were performed under nitrogen.

L-Lysine hydrochloride (30 g, 0.165 mole) was placed into the Kel-F reactor, cooled at −78° C. (dry ice acetone bath) and 80 ml of hydrogen fluoride were condensed, then removed by a fast stream of nitrogen at room temperature (thus the amino acid was converted to the HF salt and all Cl− ions were removed; presence of Cl− may result in chlorination of the amino acid in addition to fluorination). The reactor was again cooled to −78° C. and 200 ml of HF was condensed.

| Effects of Cyclichexapeptide Analogs of Somatostatin on Gastric Secretion (Dose 0.8 μg/ml./min. − infusion 060 min.) | | | | | | | | |
|---|---|---|---|---|---|---|---|---|
| | Gastric Secretion % Inhibition | | | | | | | |
| Compound | Vol. | | | | Acid Concentration | | | |
| | 0-30 | 30-60 | 60-90 | 90-120 | 0-30 | 30-60 | 60-90 | 90-120 |
| Somatostatin | 85 | 97 | 81 | 37 | 16 | 77 | 61 | 14 |
| Cyclo(Pro—Phe—D-Trp—γ-F—Lys—Thr—Phe) | 78 | 93 | 51 | (−68) | 26 | 45 | 52 | 12 |
| Cyclo(Pro—Phe—D-Trp—δ-F—Lys—Thr—Phe) | 93 | 94 | (−52) | (−172) | 28 | 22 | 19 | (−2) |

Trifluoromethylhypofluorite (19.5 g, 0.187 mole) was bubbled through the solution at −78° C. for 7 hours with simultaneous UV irradiation and stirring. The HF was blown off with a stream of nitrogen overnight; the residue (light yellow gum) was dissolved in 100 ml 2.5 N HCl and evaporated to dryness in vacuo. The residue was passed through Dowex 50-X8 ion exchange resin (H+ form, 500 ml), washed with 1 L. of water and eluted with 4 N HCl. Fractions containing the amino acid were combined and evaporated to dryness to yield 35.2 g crude fluorinated L-lysine 2 HCl. This crude product was a mixture of 5-fluoro-L-lysine 25%, and 4-fluoro-L-lysine 71% and an unidentified amino acid 4%.

The above mixture of 4- and 5-fluoro-L-lysine 2 HCl (10 g, 42 mmoles) was dissolved in 150 ml of methanol and 15 ml of dimethylsulfite was added. The solution was saturated with HCl gas at 0° C. then stirred at room temperature overnight. A crystalline precipitate was formed, filtered, washed with cold isopropanol, and dried to constant weight at 64° C. in vacuo to yield 1.72 g (16% yield) of methyl 4-fluoro-L-lysinate 2 HCl, $[\alpha]_D^{27}+14.7°$ (2% in 2.5 N HCl).

Esterification of another 24 g (101 mmoles) of fluorination mixture yielded 7.9 g (32%) of methyl 4-fluoro-L-lysinate.2 HCl, which after recrystallization from 32 ml of methanol (47% yield), gave a product with rotation $[\alpha]_D^{26}=+14.3°$ (2% in 2.5 N HCl).

Hydrolysis of the ester by heating at 95° C. for 6 hours in 10 volumes concentrated HCl yielded quantitatively 4-fluoro-L-lysine.2 HCl $[\alpha]_D^{26}+14.9°$ (2% in 2.5 N HCl) Spinco amino acid analysis and $^{19}F$ NMR indicated this was a mixture of 4-fluoro-L-lysine (77%) and 5-fluoro-L-lysine (23%).

EXAMPLE 9

γ- and δ-F-Lys(ε-CBZ)-OH

The pH of an aqueous solution (50 ml) containing γ- and δ-F-Lys.HCl (2.48 g), and copper chloride (CuCl$_2$.2H$_2$O) (0.98 g) was adjusted to 9.5 with 2 N sodium hydroxide. Benzyloxy carbonyl chloride (1.64 ml) was added and the mixture was stirred magnetically at 25° C. for 40 minutes and kept at pH 9.5 by addition of 2 N NaOH. After filtration and trituration with H$_2$O and EtOAc, the solid product was dissolved in a water-acetic acid (8:2) mixture by adjustment of the pH to 0.5 with concentrated HCL. Hydrogen sulfide was bubbled through the solution for 5 minutes, the precipitated copper sulfide (CuS) was filtered and the filtrate was evaporated in vacuo to 30 ml. The pH was adjusted to 4.5 with pyridine and the product (2.4 g) was collected by filtration. The product had an R$_f$ of 0.45 in thin layer chromatographic analysis, (60-30-4-6, chloroform-methanol-water-ammonium hydroxide) and R$_f$ 0.45 (60-30-5, chloroform-methanol-water). The nuclear magnetic resonance spectrum shows a triplet at 3.25 ppm in DMF-d$_7$-NaOD which did not change chemical shifts upon acidification.

EXAMPLE 10

α-Boc-γ- and δ-F-Lys(ε-CBZ)-OH

To a suspension of γ- and δ-F-Lys(CBZ)-OH (2.6 g) and 1.9 ml TEA in 20 ml THF-H$_2$O (1:1) was added 2-(tert-butoxycarbonyloxyimino)-2-phenylacetonitrile (Boc-ON, 2.4 g). After 20 hours at 25° C., H$_2$O (50 ml) was added and the reaction mixture was extracted with ether (3×20 ml). The aqueous layer was acidified to pH 1.2 with 10% hydrochloric acid and the oily product was extracted with ethyl acetate (3×50 ml). After drying of the combined organic layers with magnesium sulfate, filtration, and evaporation of the solvent, Boc-γ- and δ-F-Lys(CBZ)-OH (3.32 g) was obtained as a thick oil. The product mixture had an R$_f$ of 0.3 (80-20-2, chloroform-methanol-ammonium hydroxide). The infrared spectrum in chloroform-TEA showed the presence of carboxylate absorption at 6.23μ.

What is claimed is:
1. A compound having the formula:

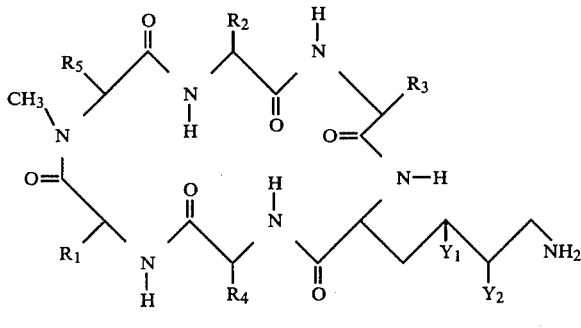

and

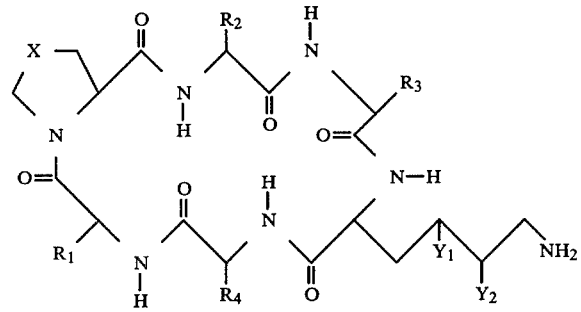

wherein
Y$_1$ and Y$_2$ are hydrogen or fluorine provided Y$_1$ and Y$_2$ are not the same;

X is (CH$_2$)$_m$ wherein m is 0, 1, or 2 or sulfur;

R$_1$ and R$_2$ are independently lower alkyl, benzyl, substituted benzyl wherein the substituent may be one or two of loweralkyl, halogen, hydroxy, amino, nitro or loweralkoxy; and loweralkyl substituted with a 5 or 6 membered heterocyclic ring;

R$_3$ is 3-indolylmethyl or substituted 3-indolylmethyl wherein the substituent may be loweralkyl, loweralkoxy or halogen;

R$_4$ is loweralkyl, hydroxyloweralkyl, benzyl, carboxyloweralkyl, aminoloweralkyl or substituted hydroxy benzyl wherein the substituent may be loweralkyl, loweralkoxy, hydroxy, halogen, amino or nitro, and R$_5$ is hydrogen, loweralkyl, benzyl, or substituted benzyl wherein the substituent is loweralkyl, loweralkoxy, hydroxy, halogen, amino or nitro.

2. A compound of claim 1 wherein
Y$_1$, Y$_2$, R$_1$ and R$_2$ are as defined in claim 1;
R$_3$ is 3-indolylmethyl or substituted indolylmethyl wherein the substituent is methoxy or fluoro; and
R$_4$ is methyl, ethyl, hydroxymethyl or hydroxyethyl; and
R$_5$ is as defined in claim 1.

3. A compound of claim 2 wherein R$_5$ is methyl.

4. A compound of claim 3 wherein:

Y is methylene;

R₁ and R₂ are as defined in claim 1;

R₃ is 3-indolylmethyl;

R₄ is hydroxyethyl; and

R₅ is methyl.

5. The compound of claim 2 which is cyclo (Pro-Phe-D-Trp-γ-F-Lys-Thr-Phe).

6. The compound of claim 2 which is cyclo (Pro-Phe-D-Trp-δ-F-Lys-Thr-Phe).

7. The compound of claim 2 which is cyclo(N-Me-Ala-Tyr-D-Trp-γ-F-Lys-Val-Phe).

8. The compound of claim 2 which is cyclo(N-Me-Ala-Tyr-D-Trp-δ-F-Lys-Val-Phe).

9. A pharmaceutical composition for inhibiting the release of glucogan, growth hormone and insulin comprising a therapeutically effective amount of the cyclic hexapeptide of claim 1 or the nontoxic acid addition salts thereof in a pharmaceutically acceptable liquid or solid carrier.

* * * * *